(12) United States Patent
Marash

(10) Patent No.: US 11,491,349 B2
(45) Date of Patent: Nov. 8, 2022

(54) PATIENT IRRADIATION TREATMENT PLAN VERIFICATION SYSTEM AND METHOD

(71) Applicant: Sino-Israeli Health Alliance International Medical Technology Co., Ltd., Shandong (CN)

(72) Inventor: Michael Marash, Kishon Le'tzion (IL)

(*) Notice: Subject to any disclaimer, the term of this patent is extended or adjusted under 35 U.S.C. 154(b) by 495 days.

(21) Appl. No.: 16/488,584

(22) PCT Filed: Jul. 15, 2018

(86) PCT No.: PCT/IL2018/050778
§ 371 (c)(1),
(2) Date: Aug. 25, 2019

(87) PCT Pub. No.: WO2019/016796
PCT Pub. Date: Jan. 24, 2019

(65) Prior Publication Data
US 2021/0170200 A1 Jun. 10, 2021

Related U.S. Application Data

(60) Provisional application No. 62/534,231, filed on Jul. 19, 2017.

(51) Int. Cl.
*G16H 20/40* (2018.01)
*A61N 5/10* (2006.01)

(52) U.S. Cl.
CPC .......... *A61N 5/1071* (2013.01); *G16H 20/40* (2018.01); *A61N 2005/1062* (2013.01); *A61N 2005/1074* (2013.01); *A61N 2005/1087* (2013.01)

(58) Field of Classification Search
CPC .... A61N 1/36128; A61N 1/3603; A61N 5/00; A61N 5/10; A61N 5/1028; A61N 5/103;
(Continued)

(56) References Cited

U.S. PATENT DOCUMENTS

| | | | | |
|---|---|---|---|---|
| 5,117,829 A * | 6/1992 | Miller | .................. | A61N 5/1049 378/65 |
| 7,684,647 B2 * | 3/2010 | Fu | .......................... | G06V 10/24 348/580 |

(Continued)

OTHER PUBLICATIONS

Moore, C. S., Avery, G., & Balcam, S. (2012). Use of a digitally reconstructed radiograph-based computer simulation for the optimisation of chest radiographic techniques for computed radiography imaging systems. The British Journal of Radiology, 85(1017), 630-639. https://doi.org/10.1259/bjr/47377285 (Year: 2012).*

(Continued)

*Primary Examiner* — Thaddeus B Cox
*Assistant Examiner* — Marc D. Honrath
(74) *Attorney, Agent, or Firm* — Jaffery Watson Mendonsa & Hamilton LLP

(57) ABSTRACT

A patient irradiation treatment plan verification system, the system constituted of: a treatment irradiation source arranged to output a treatment irradiation beam; a first detector; and a patient support member arranged to support a patient, the patient support member positioned between the treatment irradiation source and the first detector, wherein the first detector is arranged to detect the output treatment irradiation beam after the output treatment irradiation beam has irradiated the supported patient and output information regarding the detected irradiation beam.

20 Claims, 3 Drawing Sheets

(58) Field of Classification Search
CPC .. A61N 5/1031; A61N 5/1038; A61N 5/1039; A61N 5/1042; A61N 5/1048; A61N 5/1049; A61N 5/1064; A61N 5/1065; A61N 5/1067; A61N 5/1069; A61N 5/107; A61N 5/1071; A61N 5/1077; A61N 2005/1054; A61N 2005/1062; A61N 2005/1074; A61N 2005/1087; G16H 20/40
See application file for complete search history.

(56) References Cited

U.S. PATENT DOCUMENTS

| | | | |
|---|---|---|---|
| 9,616,251 B2 | 4/2017 | Filiberti et al. | |
| 2007/0181815 A1 | 8/2007 | Ebstein | |
| 2008/0031406 A1* | 2/2008 | Yan | A61N 5/1038 378/65 |
| 2009/0022383 A1* | 1/2009 | Falco | A61N 5/1049 378/65 |
| 2010/0119032 A1 | 5/2010 | Yan et al. | |
| 2012/0035462 A1* | 2/2012 | Maurer, Jr. | A61B 90/39 600/431 |
| 2015/0314140 A1* | 11/2015 | Verhaegen | A61N 5/1031 378/62 |
| 2016/0114191 A1 | 4/2016 | Sankey | |
| 2016/0287906 A1* | 10/2016 | Nord | A61N 5/1071 |
| 2017/0197099 A1* | 7/2017 | Ruebel | A61N 5/1049 |

OTHER PUBLICATIONS

TechTarget. (Aug. 14, 2019). What is processor (CPU)? A definition from whatis.com. WhatIs.com. Retrieved May 10, 2022, from https://www.techtarget.com/whatis/definition/processor (Year: 2019).*

Milickovic, N., Baltas, D., Giannouli, S., Lahanas, M., & Zamboglou, N. (2000). CT imaging based digitally reconstructed radiographs and their application in Brachytherapy. Physics in Medicine and Biology, 45(10), 2787-2800. https://doi.org/10.1088/0031-9155/45/10/305 (Year: 2000).*

International search report for parent PCT application PCT/IL2018/050778, issued by European patent office dated Nov. 30, 2018.

Written opinion on international search report for parent PCT application PCT/IL2018/050778, issued by European patent office dated Nov. 30, 2018.

* cited by examiner

PATIENT IRRADIATION TREATMENT PLAN VERIFICATION SYSTEM AND METHOD

BACKGROUND OF THE INVENTION

The invention relates generally to the field of teletherapy and in particular to a patient irradiation treatment plan image adjustment system and method.

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction. At each such fraction, care must be taken to ensure proper patient positioning, responsive to the placement markers, so as to avoid damage to organs in vicinity of the target tissue. Positioning of the patient responsive to the markers is performed based on visualization of the patient, responsive to the defined markers.

Particularly, during each fraction, the patient is positioned on a patient support member, such as a bed, in a setup position. The setup position is identical to the patient position during the imaging of the treatment planning stage, except that is in the treatment room and the center of the growth mass is positioned at the isocenter of the irradiation source. The setup position of the patient is typically verified by imaging and/or positioning devices. U.S. patent application publication S/N US 2015/0238779, published Aug. 27, 2015 to Marash et al., the entire contents of which are incorporated herein by reference, is addressed to a method of evaluating a change in radiation within a target tissue of a patient in accordance with an updated image of the patient. Although this provides a simulated verification of the irradiation dosimetry, the simulation may not be completely accurate, due to errors in conversion between the x-ray energy of the CT image and the proton energy of the treatment beam. Thus, a more accurate dosimetry verification technique is desired.

SUMMARY OF THE INVENTION

Accordingly, it is a principal object of the present invention to overcome disadvantages of prior art methods and arrangements of teletherapy. This is provided in the present invention by a patient irradiation treatment plan verification system, the system comprising: a treatment irradiation source arranged to output a treatment irradiation beam; a first detector; and a patient support member arranged to support a patient, the patient support member positioned between the treatment irradiation source and the first detector, wherein the first detector is arranged to detect the output treatment irradiation beam after the output treatment irradiation beam has irradiated the supported patient and output information regarding the detected irradiation beam.

In one embodiment, the system further comprises: a memory, having stored therein information regarding treatment irradiation dosage for the supported patient; and a control circuitry, the control circuitry arranged to: receive the irradiation beam information from the first detector, compare the received irradiation beam information to the stored irradiation dosage information, and output information responsive to the outcome of the irradiation comparison. In one further embodiment, the memory further has stored therein a 3 dimensional (3D) treatment plan image of the supported patient, wherein the control circuitry is further arranged to: map the stored dosage information to a coordinate system of the stored 3D treatment plan image; generate a first digitally reconstructed radiograph (DRR) of the stored 3D treatment plan image in a detection plane of the first detector; and project the mapped dosage information to the generated first DRR, and wherein the irradiation comparison comprises a comparison of the projected dosage information and the received irradiation beam information.

In one yet further embodiment, responsive to the irradiation comparison indicating that a dosage alignment function of a difference between the received irradiation beam information and the projected dosage information is greater than a predetermined dosage alignment value, the control circuitry is further arranged to control the treatment irradiation source to adjust the output treatment irradiation beam such that the dosage alignment difference function decreases. In another embodiment, the treatment irradiation beam is a proton beam and the first detector is a proton detector.

In one embodiment, the system further comprises: a memory having stored therein a 3 dimensional (3D) treatment plan image of the supported patient; and a control circuitry, the control circuitry arranged to: generate a first digitally reconstructed radiograph (DRR) of the stored 3D treatment plan image in a detection plane of the first detector; compare the received irradiation beam information to the generated first DRR; and responsive to the DRR comparison indicating that a first patient alignment function of a difference between the received irradiation beam information and the generated first DRR is greater than a predetermined patient alignment value, control the patient support member to adjust the position of the supported patient such that the first patient alignment difference function decreases. In one further embodiment, the memory has further stored therein a 2-dimensional (2D) image of the supported patient, and wherein the control circuitry is further arranged to: generate a second DRR of the stored 3D treatment plan image in a plane associated with the stored 2D image; compare the stored 2D image to the generated second DRR; and responsive to the outcome of the irradiation comparison indicating that a second patient alignment function of a difference between the stored 2D image and the generated second DRR is greater than a predetermined patient alignment value, control the patient support member to adjust the position of the supported patient such that the second patient alignment difference function decreases.

In another embodiment, the system further comprises: a first x-ray energy source arranged to output a first x-ray beam; a second detector arranged to receive the first x-ray beam after the first x-ray beam has irradiated the supported patient and output information regarding the detected first x-ray beam, the patient support member positioned between the second detector and the first x-ray energy source; a second x-ray energy source arranged to output a second x-ray beam; and a third detector arranged to receive the second x-ray beam after the second x-ray beam has irradiated the supported patient and output information regarding the detected second x-ray beam, the patient support member positioned between the third detector and the second x-ray energy source, wherein the treatment irradiation beam is a proton beam and the first detector is a proton detector.

In one independent embodiment, a patient irradiation treatment plan verification method is provided, the method comprising: irradiating a patient with a treatment irradiation beam; detecting the treatment irradiation beam after the treatment irradiation beam has irradiated the patient; and outputting information regarding the detected irradiation beam.

In one embodiment, the method further comprises: receiving the output irradiation beam information; comparing the received irradiation beam information to predetermined irradiation dosage information; outputting information responsive to the outcome of the irradiation comparison. In one further embodiment, the detecting of the treatment irradiation beam is performed by a first detector, the method further comprising: mapping the predetermined irradiation dosage information to a coordinate system of a 3-dimensional (3D) treatment plan image of the patient; generating a first digitally reconstructed radiograph (DRR) of the 3D treatment plan image in a detection plane of the first detector; and projecting the mapped dosage information to the generated first DRR, and wherein the irradiation comparison comprises a comparison of the projected dosage information and the received irradiation beam information.

In one yet further embodiment, responsive to the irradiation comparison indicating that a dosage alignment function of a difference between the received irradiation beam information and the projected dosage information is greater than a predetermined dosage alignment value, the method further comprises adjusting the treatment irradiation beam such that the dosage alignment difference function decreases. In another embodiment, the treatment irradiation beam is a proton beam.

In one embodiment, the detecting of the treatment irradiation beam is performed by a first detector, the method further comprising: generating a first digitally reconstructed radiograph (DRR) of a 3-dimensional (3D) treatment plan image in a detection plane of the first detector; comparing the received irradiation beam information to the generated first DRR; and responsive to the DRR comparison indicating that a first patient alignment function of a difference between the received irradiation beam information and the generated first DRR is greater than a predetermined patient alignment value, adjusting the position of the patient such that the first patient alignment difference function decreases. In one yet further embodiment, the method further comprises: generating a second DRR of the 3D treatment plan image in a plane associated with a 2-dimensional (2D) image of the patient; comparing the 2D image to the generated second DRR; and responsive to the outcome of the irradiation comparison indicating that a second patient alignment function of a difference between the 2D image and the generated second DRR is greater than a predetermined patient alignment value, adjusting the position of the patient such that the second patient alignment difference function decreases.

In another embodiment, the treatment irradiation beam is a proton beam, wherein the method further comprises: outputting a first x-ray beam; receiving the first x-ray beam after the first x-ray beam has irradiated the patient; outputting information regarding the detected first x-ray beam; outputting a second x-ray beam; receiving the second x-ray beam after the second x-ray beam has irradiated the patient; and outputting information regarding the detected second x-ray beam.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
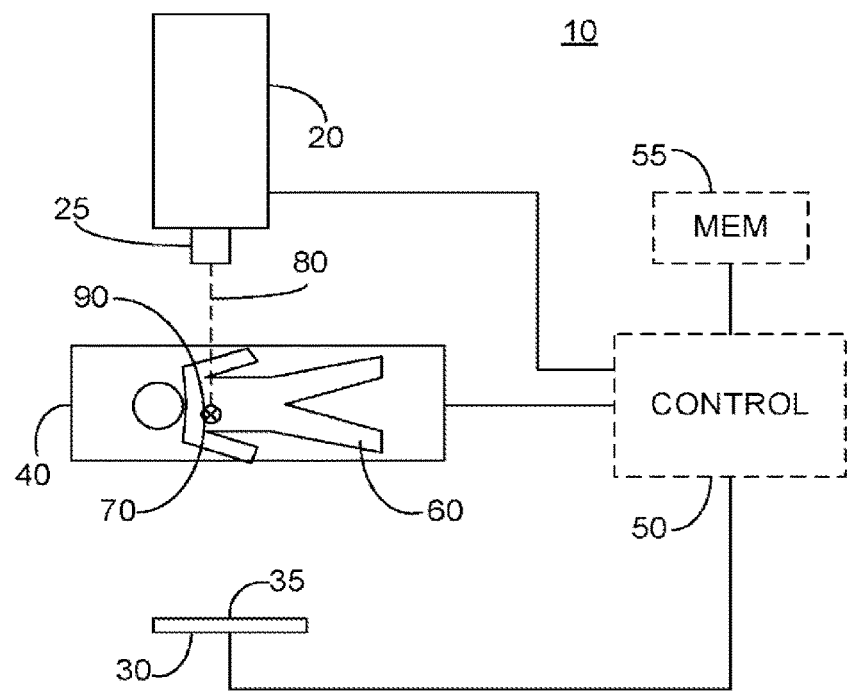
FIG. 1 illustrates a high level schematic diagram of a first embodiment of a patient irradiation treatment plan verification system.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level schematic diagram of a patient irradiation treatment plan verification system 10. Patient irradiation treatment plan verification system 10 comprises: a treatment irradiation source 20 exhibiting a nozzle 25; a detector 30, exhibiting a detection plane 35; a patient support member 40; an optional control circuitry 50; and an optional memory 55. Patient support member 40 has supported thereon a patient 60 exhibiting a treatment area 70. Treatment irradiation source 20 is, in one embodiment, a proton irradiation source, and is described herein as such, however this is not meant to be limiting in any way and any type of irradiation source suitable for teletherapy can be used without exceeding the scope. Similarly, detector 30 is, in one embodiment, a proton detector, and is described herein as such, however this is not meant to be limiting in any way. Particularly, the type of detector 30 is selected to match the type of energy output by treatment irradiation source 20. In one embodiment, treatment irradiation source 20 is a fixed beam irradiation source, i.e. it is maintained in a fixed positioned and not translatable or rotatable by means of a gantry or similar mechanism. Detector 30 and treatment irradiation source 20 are positioned on opposing sides of patient support member 40 such that detector 30 faces nozzle 25. Optional control circuitry 50 is in communication with treatment irradiation source 20, detector 30 and patient support member 40. In one embodiment, optional memory 55 has stored therein a 3-dimensional (3D) treatment planning image of patient 60. Particularly, the treatment planning image is an image of patient 60 in relation to nozzle 25 of treatment irradiation source 20 such that treatment area 70 of patient 60 is positioned at the isocenter of treatment irradiation source 20, as will be described below. In one further embodiment, the 3D treatment planning image is a computed tomography (CT) image.

In operation, patient support member 40 is positioned such that treatment area 70 of patient 60 is positioned at the isocenter of the beams of treatment irradiation source 20, in accordance with a predetermined treatment plan. Optionally, patient support member 40 is controlled by optional control circuitry 50 responsive to the 3D image of patient 60 stored in optional memory 55 such that patient 60 is properly positioned. After patient 60 is positioned in relation to nozzle 25 of treatment irradiation source 20 in accordance with the treatment plan, and optionally after verification of the positioning of patient 60, as will be described below, treatment irradiation source 20 outputs a treatment irradiation beam 80 from nozzle 25 which irradiates treatment area 70 of patient 60. Optionally, the generation of treatment irradiation beam 80 is control by optional control circuitry 50. Treatment irradiation beam 80 comprises a plurality of proton beams which exhibit an isocenter 90, isocenter 90 being centered on treatment area 70. In one embodiment, treatment irradiation beam 80 exhibits an intensity of at least 50 mega-electron-volts (MeV). After irradiating patient 60, the protons of treatment irradiation beam 80 are detected by detector 30. The portion of detector 30 which detects the protons defines detection plane 35. Information regarding the number of protons received at each pixel of detector 30 is output. The output information can be used to verify irradiation dosimetry for patient 60, and further optionally verify positioning of patient 60 in relation to nozzle 25 of treatment irradiation source 20, as will be described below.

Figure 2:
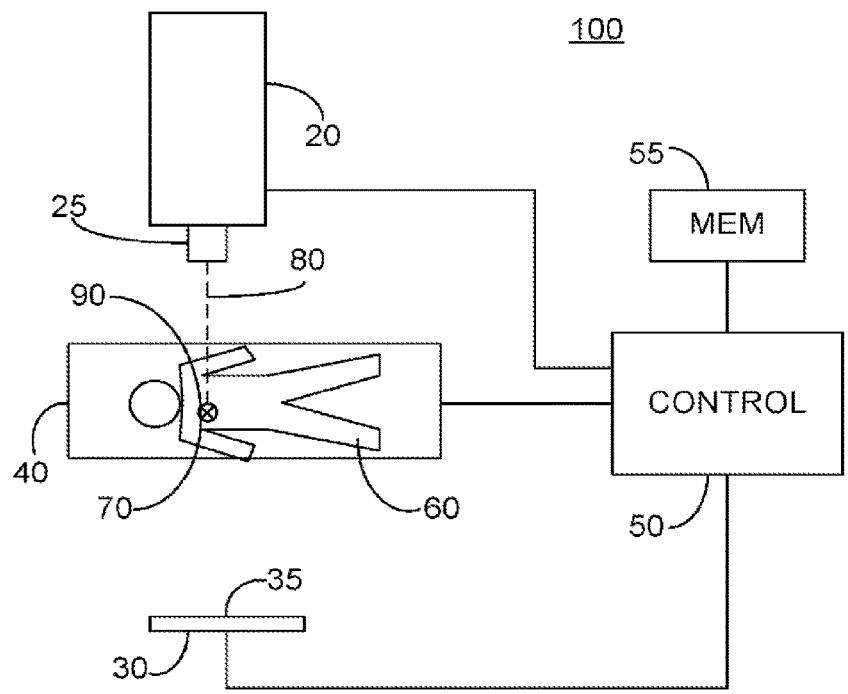
FIG. 2 illustrates a high level schematic diagram of a second embodiment of a patient irradiation treatment plan verification system.

FIG. 2 illustrates a high level schematic diagram of a patient irradiation treatment plan verification system 100. Patient irradiation treatment plan verification system 100 comprises: a treatment irradiation source 20 exhibiting a nozzle 25; a detector 30 exhibiting a detection plane 35; a patient support member 40; a control circuitry 50; and a memory 55. As described above, memory 55 has stored therein a 3D image of patient 60 in a treatment planning position. Memory 55 further has stored therein information regarding treatment irradiation dosage for patient 60, i.e. irradiation dosage values for treatment area 70 of patient 60. Patient support member 40 has supported thereon a patient 60 exhibiting a treatment area 70. Detector 30 and treatment irradiation source 20 are positioned on opposing sides of patient support member 40 such that detector 30 faces nozzle 25. Control circuitry 50 is in communication with treatment irradiation source 20, detector 30 and patient support member 40.

In operation, patient support member 40 is positioned such that treatment area 70 of patient 60 is positioned at the isocenter of the beams of treatment irradiation source 20, in accordance with the predetermined treatment plan. After patient 60 is positioned in relation to nozzle 25 of treatment irradiation source 20 in accordance with the treatment plan, and optionally after verification of the positioning of patient 60, as will be described below, control circuitry 50 controls treatment irradiation source 20 to output treatment irradiation beam 80 from nozzle 25 such that treatment area 70 of patient 60 is irradiated with treatment irradiation beam 80. Specifically, isocenter 90 of treatment irradiation beam 80 is positioned at treatment area 70. Treatment irradiation beam 80 exhibits a predetermined irradiation intensity in accordance with the predetermined treatment plan. In one embodiment, before treatment is initiated, control circuitry 50 controls treatment irradiation source 20 to output a lower intensity treatment irradiation beam 80, preferably exhibiting an intensity of at least 50 MeV, to thereby irradiate treatment area 70 of patient 60. After irradiating patient 60, either with the full intensity or lower intensity treatment irradiation beam 80, the protons of treatment irradiation beam 80 are detected by detector 30. The portion of detector 30 which detects the protons defines detection plane 35. Information regarding the number of protons received at each pixel of detector 30 is output to control circuitry 50.

Control circuitry 50 generates a digitally reconstructed radiograph (DRR) from the 3D image of patient 60 stored in memory 55 in detection plane 35 of detector 30. Particularly, the DRR is a 2-dimensional (2D) image of patient 60 in relation to nozzle 25, as seen from the angle of detection plane 35. Additionally, control circuitry 50 maps the dosage information stored in memory 55 to the coordinate system of the stored 3D image such that the planned irradiation dosage for each voxel of the 3D image is derived. Control circuitry 50 then projects the mapped dosage information to the detection plane 35 DRR such that the planned irradiation dosage for each pixel of the DRR is derived. Control circuitry 50 compares the received information regarding the number of protons received at each pixel of detector 30 to the DRR projected dosage information. In one embodiment, control circuitry 50 determines the percentage of protons which should be absorbed by patient 60 at each pixel of the DRR, in accordance with the treatment plan, and further determines the number of protons which should arrive at detector 30 according to the treatment plan, i.e. the number of protons in treatment irradiation beam 80 minus the number of protons expected to be absorbed by patient 60 in accordance with the dosage information. Control circuitry 50 then compares the number of protons received at each pixel of detector 30 to the determined number of protons which should arrive at each pixel of detector 30, after irradiation of treatment area 70 with treatment irradiation beam 80, in accordance with the treatment plan.

In another embodiment, control circuitry 50 determines a dosage alignment function of a difference between the received proton information and the DRR projected dosage information. In one further embodiment, the dosage alignment function is an average of the differences between the number of protons received at each pixel of detector 30 and the number of protons which are determined to arrive at each pixel of detector 30 in accordance with the treatment plan, as described above.

In one embodiment, in the event that the receive proton information does not match the planned irradiation dosage, within a predetermined margin, control circuitry 50 adjusts the intensity of treatment irradiation beam 80 such that the actual dosage provided by treatment irradiation beam 80 is in accordance with the planned treatment dosage. In the embodiment where a dosage alignment difference function is determined, which is determined to be greater than a predetermined dosage alignment value, control circuitry 50 adjusts the intensity of treatment irradiation beam 80 such that the dosage alignment difference function decreases to below the predetermined dosage alignment value. As described above, in one embodiment, the dosage is verified by using a low intensity treatment irradiation beam 80 prior to initiating the treatment irradiation. In such an embodiment, after adjusting the irradiation intensity of treatment irradiation beam 80, or after confirming that the dosage provided by treatment irradiation beam 80 is correct, control circuitry 50 controls treatment irradiation source 20 to irradiate treatment area 70 of patient 60 at the predetermined intensity of the treatment plan. In the embodiment where the dosage is verified during treatment at the intensity of the treatment plan, any adjustments of the intensity are performed by control circuitry 50 during the irradiation of treatment area 70 by treatment irradiation beam 80.

In another embodiment, in the event that the received proton information does not match the planned irradiation dosage, within the predetermined margin, control circuitry 50 outputs a signal indicating that treatment irradiation beam 80 does not match the planned irradiation dosage. In the event that the received proton information matches the planned irradiation dosage, control circuitry 50 outputs a signal indicating the planned irradiation dosage is met.

In one embodiment, prior to the verification of irradiation dosage, as described above, detector 30 is utilized to verify the positioning of patient 60 in relation to nozzle 25 of treatment irradiation source 20. Particularly, as described above, control circuitry 50 controls treatment irradiation source 20 to output a low intensity treatment irradiation beam 80, preferably exhibiting an intensity greater than 50 MeV, towards treatment area 70 of patient 60. As described above, detector 30 detects protons from treatment irradiation beam 80 and outputs information regarding the received protons to control circuitry 50. Control circuitry 50 derives an image of patient 60 from the received proton information. As described above, control circuitry 50 generates a DRR of the 3D image of patient 60 in detection plane 35. The image of patient 60 derived from the proton information received from detector 30 is compared by control circuitry 50 to the DRR generated in detection plane 35 to determine whether the images of patient 60 are aligned. In one embodiment, the proton derived image and the DRR are compared pixel by pixel to determine the difference in positioning of each point on patient 60 in relation to nozzle 25 of treatment irradiation source 20.

In one embodiment, control circuitry 50 determines a first patient alignment function of the position differences between the pixels of the DRR and the pixels of the proton derived image. In one further embodiment, the first patient alignment function is an angle between a contour of patient 60 on the proton derived image and the corresponding contour on the DRR. In another further embodiment, the first patient alignment function is an average distance between the position of the pixels representing patient 60 on the proton derived image and the position of the pixels representing patient 60 on the DRR.

In the event that control circuitry 50 determines that the proton derived image of patient 60 does not match the image of patient 60 in the DRR, within a predetermined margin, e.g. in the event that the first patient alignment function is greater than a predetermined alignment value, control circuitry 50 controls patient support member 40 to adjust the position of patient 60 in relation to nozzle 25 such that the images of patient 60 become more aligned. As a result, patient 60 becomes more aligned with the predetermined treatment plan. In one embodiment, the position of patient 60 is adjusted such that the first patient alignment difference function decreases. Specifically, in the embodiment where the first patient alignment function is an angle between the contour of patient 60 on the proton derived image and the contour of patient 60 on the DRR, the position of patient 60 is adjusted such that the angle decreases. In the embodiment where the first patient alignment function is an average distance between the position of pixels of patient 60 on the proton derived image and the position of the corresponding pixels on the DRR, the position of patient 60 is adjusted such that the distance decreases.

In one embodiment, as described below, further images are utilized to verify and correct the position of patient 60. Particularly, a first 2D image of patient 60 is received and optionally stored on memory 55. The first 2D image is in a plane which exhibits a different angle with nozzle 25 than detection plane 35. In one embodiment, as will be described below, control circuitry 50 controls a 2D imager to generate the first 2D image. Control circuitry 50 generates a second DRR of the 3D image of patient 60 in the plane of the first 2D image. Control circuitry 50 compares the first 2D image of patient 60 to the second DRR to determine whether the images of patient 60 are aligned. As described above in relation to the proton derived image of patient 60, in the event that the first 2D image of patient 60 and the second DRR of patient 60 are not aligned, within a predetermined margin, control circuitry 50 controls patient support member 40 to adjust the position of patient 60 accordingly. In one embodiment, a second patient alignment function of a difference between the first 2D image of patient 60 and the second DRR of patient 60 is determined. In one further embodiment, the second patient alignment function is an angle between a contour of the patient in the first 2D image and the generated second DRR. In another embodiment, the second patient alignment function is an average distance between the position of the pixels representing the patient in the first 2D image and the position of the pixels representing the patient of the generated second DRR.

In another embodiment, as will be described below, a second 2D image of patient 60 is additionally received and optionally stored on memory 55. The second 2D image is in a plane which exhibits a different angle with nozzle 25 than the plane of the first 2D image and detection plane 35. In one embodiment, as will be described below, control circuitry 50 controls a respective 2D imager to generate the second 2D image. Control circuitry 50 generates a third DRR of the 3D image of patient 60 in the plane of the second 2D image. Control circuitry 50 compares the second 2D image of patient 60 to the third DRR to determine whether the images of patient 60 are aligned. As described above in relation to the proton derived image of patient 60, in the event that the second 2D image of patient 60 and the third DRR of patient 60 are not aligned, within a predetermined margin, control circuitry 50 controls patient support member 40 to adjust the position of patient 60 accordingly. In one embodiment, a third patient alignment function of a difference between the second 2D image of patient 60 and the third DRR of patient 60 is determined. In one further embodiment, the third patient alignment function is an angle between a contour of the patient in the second 2D image and the generated third DRR. In another embodiment, the third patient alignment function is an average distance between the position of the pixels representing the patient in the second 2D image and the position of the pixels representing the patient of the generated third DRR.

Advantageously, the position of patient 60 in relation to nozzle 25 is verified at three separate angles.

In one embodiment, in the event that it is determined that patient 60 is properly positioned, the proton information received from detector 30 is utilized to verify the dosage of irradiation treatment beam 80, as described above.

Figure 3:
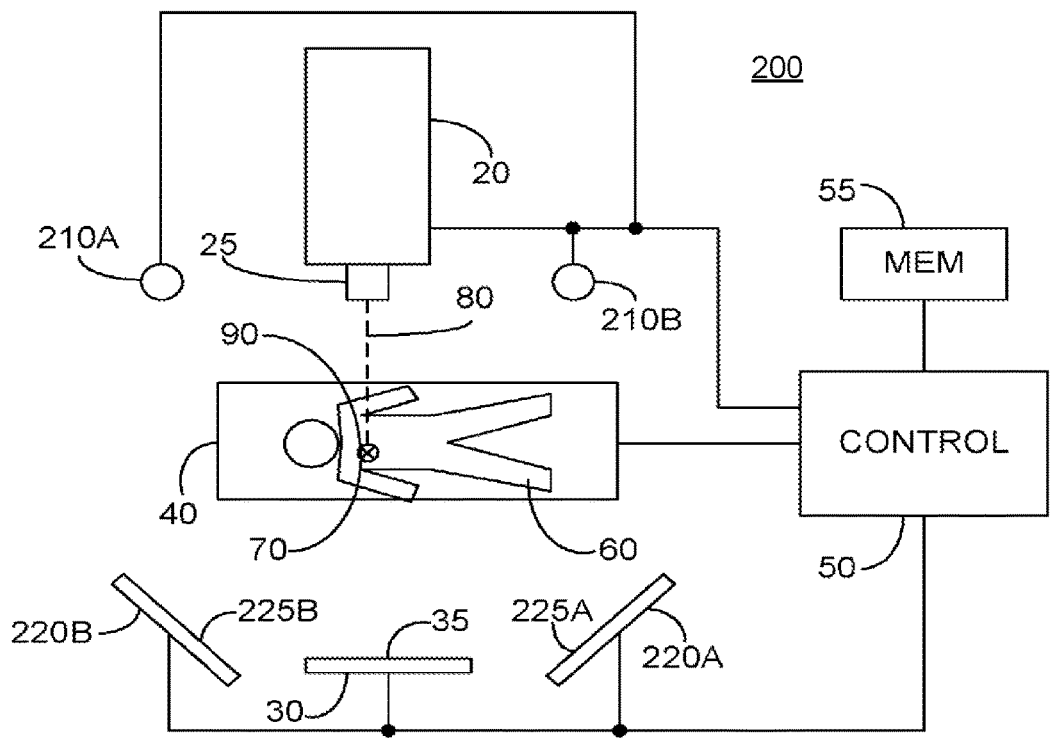
FIG. 3 illustrates a high level schematic diagram of a third embodiment of a patient irradiation treatment plan verification system.

FIG. 3 illustrates a high level schematic diagram of a patient irradiation treatment plan verification system 200. Patient irradiation treatment plan verification system 200 is in all respects similar to patient irradiation treatment plan verification system 100 with the addition of: a pair of x-ray imagers 210A and 210B; and a pair of x-ray detectors 220A and 220B, each exhibiting a detection plane 225A and 225B, respectively. X-ray imager 210A and x-ray detector 220A are positioned on opposing sides of patient support member 40 such that x-ray detector 220A faces x-ray imager 210A. Similarly, x-ray imager 210B and x-ray detector 220B are positioned on opposing sides of patient support member 40 such that x-ray detector 220B faces x-ray imager 210B.

In one embodiment, x-ray detectors 220A and 220B exhibit a generally 90 degree angle with each other. In another embodiment, detectors 30, 220A and 220B are positioned on one side of patient support member 40 and imagers 210A and 210B are positioned on the same side of patient support member 40 as irradiation treatment source 20. In one further embodiment, x-ray detectors 220A and 220B exhibit a 90 degree angle with each other, and each further exhibit a generally 45 degree angle with detector 30. In one embodiment (not shown), detector 30, x-ray detector 220A and x-ray detector 220B are each connected to a single translation mechanism which is arranged to translate the detectors vertically when not needed so as not interfere with the treatment. Each of x-ray imager 210A, x-ray imager 210B, x-ray detector 220A and x-ray detector 220B is in communication with control circuitry 50.

In operation, control circuitry 50 controls each of x-ray imager 210A and 210B to image patient 60. The x-rays are received by respective x-ray detectors 220A and 22B, and respective first and second x-ray images of patient 60 are received by control circuitry 50, as described above. As further described above, a third image of patient 60 is received from detector 30. The three images of patient 60 are compared to respective DRRs of the stored 3D image of patient 60 to verify the positioning of patient 60, as described above. Particularly, a first DRR is generated in detection plane 35 of detector 30, a second DRR is generated in detection plane 225A of x-ray detector 220A and a third DRR is generated in detection plane 225B of x-ray detector 220B. As further described above, the dosage provided by irradiation treatment beam 80 is verified responsive to proton information received from detector 30.

Figure 4:
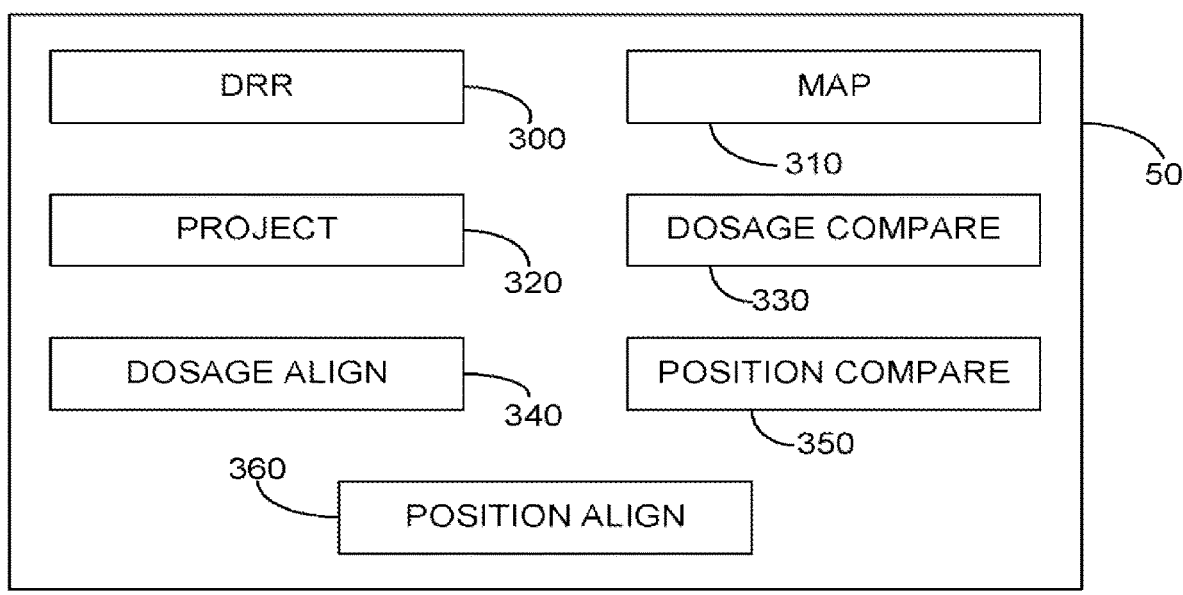
FIG. 4 illustrates a high level block diagram of an embodiment of a control circuitry for the patient irradiation treatment plan verification systems of FIGS. 1-3.

FIG. 4 illustrates a high level block diagram of an embodiment of control circuitry 50. Control circuitry 50 comprises: a DRR functionality 300; a mapping functionality 310; a projection functionality 320; a dosage comparison functionality 330; a dosage alignment functionality 340; a position comparison functionality 350; and a position alignment functionality 360. Each of DRR functionality 300, mapping functionality 310, projection functionality 320, dosage comparison functionality 330, dosage alignment functionality 340, position comparison functionality 350 and position alignment functionality 360 are implemented by any of: a unique hardware module; and a software module implemented responsive to instructions stored on memory 55 (not shown).

DRR functionality 300 is arranged to determine DRRs of the 3D image of patient 60 (not shown), as described above. Mapping functionality 310 is arranged to map irradiation dosage information to the coordinates of the 3D image, as described above. Projection functionality 320 is arranged to project the mapped irradiation dosage information to the respective DRR, as described above. Dosage comparison functionality 330 is arranged to compare the actual dosage detected by detector 30 (not shown) to the planned dosage projected to the respective DRR, as described above. Dosage alignment functionality 340 is arranged to adjust the intensity of treatment irradiation source 80 (not shown) in the event that the actual dosage does not match the planned dosage, as described above. Position comparison functionality 350 is arranged to compare, for each of the detectors, the respective image of patient 60 to the respective DRR, as described above. Position alignment functionality is arranged to control patient support member 40 (not shown) to adjust the position of patient 60 in relation to nozzle 25 (not shown) in the event that the position of patient 60 does not match the planned position, as described above.

Figure 5:
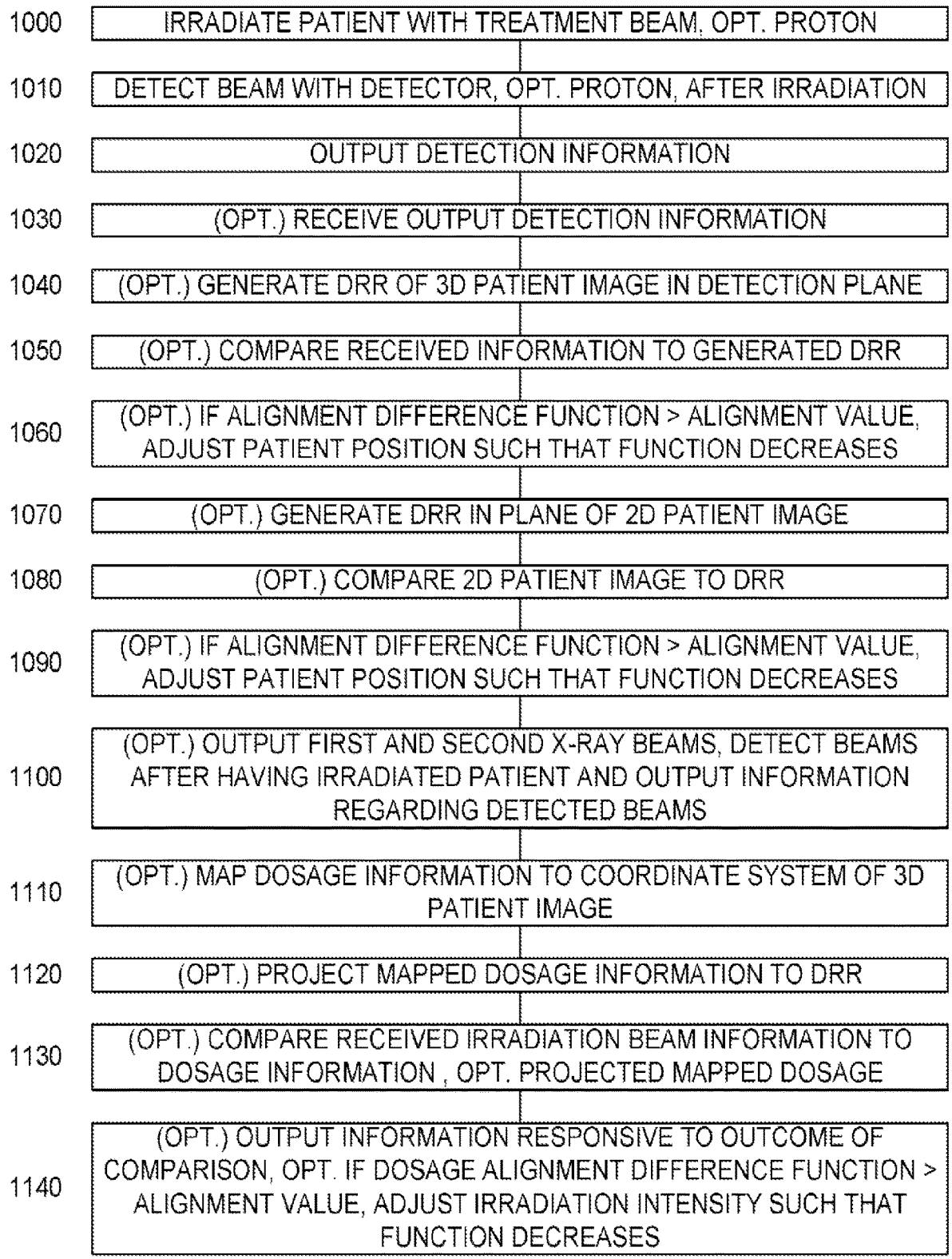
FIG. 5 illustrates a high level flow chart of a patient irradiation treatment plan verification method, according to certain embodiments.

FIG. 5 illustrates a high level flow chart of a patient irradiation treatment plan verification method, according to certain embodiments. In stage 1000, a patient is irradiated with a treatment irradiation beam. Optionally, the treatment irradiation beam is a proton beam, preferably exhibiting an intensity of at least 50 MeV. In stage 1010, the treatment irradiation beam of stage 1000 is detected by a first detector after having irradiated the patient, optionally by a proton detector. In stage 1020, information regarding the detected irradiation beam of stage 1010 is output.

In optional stage 1030, the output irradiation beam information of stage 1020 is received. In optional stage 1040, a first DRR of a 3D treatment plan image of the patient of stage 1000 is generated in a detection plane of the first detector of stage 1010. In optional stage 1050, the received irradiation beam information of optional stage 1030 is compared to the generated first DRR of optional stage 1040. In optional stage 1060, responsive to the DRR comparison of optional stage 1050 indicating that a first patient alignment function of a difference between the received irradiation beam information of optional stage 1030 and the generated first DRR of optional stage 1040 is greater than a predetermined patient alignment value, the position of the patient of stage 1000 is adjusted, in relation to a treatment irradiation source, such that the first patient alignment difference function decreases. In one embodiment, the first patient alignment function is an angle between a contour of the patient in the received information of optional stage 1030 and the corresponding contour on the generated first DRR of optional stage 1040. In another embodiment, the first patient alignment function is an average distance between the position of the pixels representing the patient in the received information of optional stage 1030 and the position of the pixels representing the patient of the generated first DRR.

In optional stage 1070, a second DRR of the 3D treatment plan image of optional stage 1040 is generated in a plane associated with a 2D image of the patient of stage 1000. In optional stage 1080, the 2D image of optional stage 1070 is compared to the generated second DRR. In optional stage 1090, responsive to the outcome of the irradiation comparison indicating that a second patient alignment function of a difference between the 2D image and the generated second DRR is greater than a predetermined patient alignment value, the position of the patient is adjusted such that the second patient alignment difference function decreases. In one embodiment, the second patient alignment function is an angle between a contour of the patient in the 2D image and the corresponding contour on the generated second DRR. In another embodiment, the second patient alignment function is an average distance between the position of the pixels representing the patient in the 2D image and the position of the pixels representing the patient of the generated second DRR.

In optional stage 1100, a first and a second x-ray beam are output. The output x-ray beams are detected after having irradiated the patient of stage 1000. Information regarding the detected first and second x-ray beams are output. In one embodiment, the first and second x-ray beam each provide a respective 2D image of the patient and the respective 2D image is compared to a respective DRR of the 3D image of the patient of optional stage 1040, in the plane of a respective x-ray detector, to determine whether the positioning of the patient is correct and matches the 3D image.

In optional stage 1110, predetermined irradiation dosage information is mapped to a coordinate system of the 3D treatment plan image of the patient of optional stage 1040. Particularly, the predetermined irradiation dosage information is the dosage information from the irradiation treatment plan. In optional stage 1120, the mapped dosage information of optional stage 1110 is projected to the generated first DRR of optional stage 1040 such that the expected percentage of energy from the treatment irradiation beam of stage 1000 to reach the detector of stage 1010 can be determined.

In optional stage 1130, the received irradiation beam information of optional stage 1030 is compared to predetermined irradiation dosage information. Optionally, the irradiation comparison comprises a comparison of the projected dosage information of optional stage 1120 and the received irradiation beam information of stage 1010. In one embodiment, the energy intensity detected by the detector is compared to the determined energy intensity which is expected to arrive at the detector in accordance with the treatment plan. In optional stage 1140, information responsive to the outcome of the irradiation comparison of optional stage 1130 is output. In one embodiment, responsive to the irradiation comparison of optional stage 1130 indicating that a dosage alignment function of a difference between the received irradiation beam information and the projected dosage information is greater than a predetermined dosage alignment value, the treatment irradiation beam of stage 1000 is adjusted such that the dosage alignment difference function decreases. Optionally, the dosage alignment difference function is an average of the differences between the energy intensity received at each pixel of the detector of stage 1010 and the expected energy intensity at the respective pixel in accordance with the treatment plan.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A patient irradiation treatment plan verification system comprising:
   a treatment irradiation source arranged to output a treatment irradiation beam;
   a first detector;
   a patient support member arranged to support a patient, said patient support member positioned between said treatment irradiation source and said first detector, wherein said first detector is arranged to detect said output treatment irradiation beam after said output treatment irradiation beam has irradiated the supported patient and output irradiation beam information regarding said detected irradiation beam; and
   a control circuitry arranged to:
      map dosage information regarding treatment irradiation dosage for the supported patient to a coordinate system of a 3-dimensional (3D) treatment plan image of the supported patient;
      generate a first digitally reconstructed radiograph (DRR) of said 3D treatment plan image in a detection plane of said first detector;
      project said mapped dosage information to said generated first DRR to derive planned irradiation dosage for each pixel of the first DRR, wherein said mapped dosage information comprises planned irradiation dosage for each voxel of the 3D treatment plan image of the supported patient;
      receive said irradiation beam information from said first detector;

compare said projected dosage information to said received irradiation beam information, wherein the comparison comprises the planned irradiation dosage for each pixel of the first DRR to the number of protons received at each pixel of said first detector; and control said treatment irradiation source to adjust said treatment irradiation beam based on the comparison.

2. The system of claim 1, further comprising: a memory that stores the information regarding treatment irradiation dosage for the supported patient wherein said control circuitry is further arranged to: output information responsive to an outcome of a comparison of said received irradiation beam information to said information regarding treatment irradiation dosage for the supported patient.

3. The system of claim 2, wherein said memory further stores the 3D treatment plan image of the supported patient.

4. The system of claim 1, wherein, to control said treatment irradiation source to adjust said treatment irradiation beam based on the comparison, the control circuitry is further arranged to:

responsive to determining that a dosage alignment function of a difference between said received irradiation beam information and said projected dosage information is greater than a predetermined dosage alignment value, control said treatment irradiation source to adjust an intensity of said output treatment irradiation beam such that said dosage alignment difference function decreases to below the predetermined dosage alignment value.

5. The system of claim 1, wherein said treatment irradiation beam is a proton beam and said first detector is a proton detector.

6. The system of claim 1, wherein said control circuitry is arranged to: compare said received irradiation beam information to said generated first DRR to determine a difference between said received irradiation beam information and said generated first DRR; and responsive to determining that a first patient alignment function of a difference between said received irradiation beam information and said generated first DRR is greater than a predetermined patient alignment value, control said patient support member to adjust the position of the supported patient such that said first patient alignment difference function decreases.

7. The system of claim 6, further comprising a memory that stores a 2-dimensional (2D) image of the supported patient, and wherein said control circuitry is further arranged to: generate a second DRR of said 3D treatment plan image in a plane associated with said stored 2D image; compare said stored 2D image to said generated second DRR to determine a difference between said stored 2D image and said generated second DRR; and responsive to determining that a second patient alignment function of the difference between said stored 2D image and said generated second DRR is greater than the predetermined patient alignment value, control said patient support member to adjust the position of the supported patient such that said second patient alignment difference function decreases.

8. The system of claim 6, wherein the first patient alignment function indicates an angle between a contour of the patient in the received irradiation beam information and a corresponding contour on the generated first DRR or an average distance between positions of pixels representing the patient in the received irradiation beam information and positions of pixels representing the patient of the generated first DRR.

9. The system of claim 1, further comprising: a first x-ray energy source arranged to output a first x-ray beam; a second detector arranged to detect said first x-ray beam after said first x-ray beam has irradiated the supported patient and output information regarding said detected first x-ray beam, said patient support member positioned between said second detector and said first x-ray energy source; a second x-ray energy source arranged to output a second x-ray beam; and a third detector arranged to detect said second x-ray beam after said second x-ray beam has irradiated the supported patient and output information regarding said detected second x-ray beam, said patient support member positioned between said third detector and said second x-ray energy source, wherein said treatment irradiation beam is a proton beam and said first detector is a proton detector.

10. The system of claim 1, wherein, to control said treatment irradiation source to adjust said treatment irradiation beam based on the comparison, the control circuitry is further arranged to:

adjust an intensity of said treatment irradiation beam such that an actual dosage provided by said treatment irradiation beam is in accordance with the planned irradiation dosage, wherein the comparison indicates that the received irradiation beam information does not match the planned irradiation dosage within a predetermined margin.

11. The system of claim 10, wherein the control circuitry is further arranged to output a signal indicating that treatment irradiation beam does not match the planned irradiation dosage, wherein the comparison indicates that the received irradiation beam information does not match the planned irradiation dosage within the predetermined margin.

12. The system of claim 1, wherein the control circuitry is further arranged to control said patient support member to adjust the position of the supported patient based on the comparison.

13. A patient irradiation treatment plan verification method, the method comprising:

irradiating, by a treatment irradiation source, a patient with a treatment irradiation beam;

detecting, by a first detector, the treatment irradiation beam after said treatment irradiation beam has irradiated the patient;

outputting irradiation beam information regarding said detected irradiation beam;

mapping, by a control circuitry, dosage information regarding treatment irradiation dosage for the patient to a coordinate system of a 3-dimensional (3D) treatment plan image of the patient;

generating, by the control circuitry, a first digitally reconstructed radiograph (DRR) of said 3D treatment plan image in a detection plane of said first detector;

projecting said mapped dosage information to said generated first DRR to derive planned irradiation dosage for each pixel of the first DRR, wherein said mapped dosage information comprises planned irradiation dosage for each voxel of the 3D treatment plan image of the supported patient;

comparing said projected dosage information to said irradiation beam information, comprising:

comparing the planned irradiation dosage for each pixel of the first DRR to the number of protons detected at each pixel of said first detector; and controlling said treatment irradiation source to adjust said treatment irradiation beam based on the comparison.

14. The method of claim 13, further comprising:
outputting information responsive to an outcome of the comparison of said received irradiation beam information to said information regarding treatment irradiation dosage for the supported patient.

15. The method of claim 14, the method further comprising:
storing the 3D treatment plan image of the patient in a memory.

16. The method of claim 13, wherein controlling said treatment irradiation source to adjust said treatment irradiation beam based on the comparison comprises responsive to determining that a dosage alignment function of a difference between said irradiation beam information and said projected dosage information is greater than a predetermined dosage alignment value, adjusting an intensity of the treatment irradiation beam such that said dosage alignment difference function decreases to below the predetermined dosage alignment value.

17. The method of claim 13, wherein the treatment irradiation beam is a proton beam.

18. The method of claim 13, the method further comprising:
comparing said irradiation beam information to said generated first DRR; and
responsive to determining that a first patient alignment function of a difference between said irradiation beam information and said generated first DRR is greater than a predetermined patient alignment value, adjusting a position of the patient such that said first patient alignment difference function decreases.

19. The method of claim 18, further comprising:
generating a second DRR of the 3D treatment plan image in a plane associated with a 2-dimensional (2D) image of the patient;
comparing the 2D image to said generated second DRR to determine a difference between said 2D image of the patient and said generated second DRR; and
responsive to determining that a second patient alignment function of the difference between the 2D image and said generated second DRR is greater than the predetermined patient alignment value, adjusting the position of the patient such that said second patient alignment difference function decreases.

20. The method of claim 13, wherein the treatment irradiation beam is a proton beam, the method further comprising:
outputting a first x-ray beam;
receiving said first x-ray beam after said first x-ray beam has irradiated the patient;
outputting information regarding said received first x-ray beam;
outputting a second x-ray beam;
receiving said second x-ray beam after said second x-ray beam has irradiated the patient; and
outputting information regarding said received second x-ray beam.

* * * * *